(12) United States Patent
Springer et al.

(10) Patent No.: US 8,231,860 B2
(45) Date of Patent: Jul. 31, 2012

(54) DIAGNOSTIC MICROSPHERES

(75) Inventors: Chaim Springer, Jerusalem (IL);
Avraham Avital, Mevasseret Zion (IL);
Theodor Stern, Jerusalem (IL); Shimon Benita, Mevasseret Zion (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 1168 days.

(21) Appl. No.: 10/522,200

(22) PCT Filed: Jul. 3, 2003

(86) PCT No.: PCT/IL03/00552
§ 371 (c)(1),
(2), (4) Date: Apr. 22, 2005

(87) PCT Pub. No.: WO2004/011035
PCT Pub. Date: Feb. 5, 2004

(65) Prior Publication Data
US 2005/0214216 A1    Sep. 29, 2005

(30) Foreign Application Priority Data
Jul. 25, 2002    (IL) .......................................... 150906

(51) Int. Cl.
*A61K 49/00*    (2006.01)
(52) U.S. Cl. ....................................................... 424/9.1
(58) Field of Classification Search .................. None
See application file for complete search history.

(56) References Cited

U.S. PATENT DOCUMENTS

| 5,205,290 A | * | 4/1993 | Unger ........................... 424/489 |
| 5,665,383 A | | 9/1997 | Grinstaff et al. |
| 2001/0010824 A1 | | 8/2001 | Handjani et al. |

FOREIGN PATENT DOCUMENTS

| EP | 0 804 932 A | 11/1997 |
| WO | WO 98/07410 A | 2/1998 |

OTHER PUBLICATIONS

Avital et al., "Charcoal is a sensitive, specific, and stable marker for the diagnosis of aspiration in hamsters," Pediatric Research, Mar. 2002, pp. 397-401, vol. 51, No. 3.*
Joon Oh et al. "Assessment of Biodegradability of Polymeric Microspheres in vivo: Poly(DL-lactic acid), poly(L-lactic acid) and poly(DL-lactide-co-glycolide) microspheres", Arch. Pharm. Res. vol. 16, No. 4, pp. 312-317, 1993.*
Yasuhiko et al Phagocytosis of polymer microspheres by macrophages, Book, Advances in polymer Sciences, vol. 94, ISSN 0065-3195, 1990.*
Rajeev "The manufacturing techniques of various drug loaded biodegradables poly(lactide-co-glycolide) (PGLA) device", Biomaterials vol. 21, 2000, pp. 2475-2490 and.*
Tabata et al, "Macrophage phatocytosis of biodegradable microspheres composed of L-lactic acid/glycolic acid homo and copolymers", J. Biomed. Res. 1988, vol. 22, No. 10, pp. 837-858.*

(Continued)

*Primary Examiner* — Brandon Fetterolf
*Assistant Examiner* — Jean Cornet
(74) *Attorney, Agent, or Firm* — Browdy and Neimark, PLLC

(57) ABSTRACT

The invention provides a diagnostic composition for detecting both aspiration and gastroesophageal reflux comprising bio-degradable microspheres having a diameter of about 0.1-10 microns.

6 Claims, 2 Drawing Sheets

Polylactic acid instilled animal

OTHER PUBLICATIONS

Springer and Avital, Simple and specific test for the diagnosis of aspiration into the airways using a corn flour-milk mixture in a hamster model, Pediatric Pulmonology, 35(5):400-4 (May 2003) Abstract Only.

Avital et al., "Charcoal is a sensitive, specific, and stable marker for the diagnosis of aspiration in hamsters," *Pediatric Research*. Mar. 2002, pp. 397-401, vol. 51, No. 3.

Avital et al., "Polystyrene microspheres as a specific marker for the diagnosis of aspiration in hamsters," *American Journal of Respiratory Cell and Molecular Biology*, Oct. 2002, pp. 511-514, vol. 27, No. 4.

Corwin et al., "The Lipid-Laden Alveolar Macrophage as a Marker of Aspiration in Parenchymal Lung Disease," Database Biosis 'Online! Biosciences Information Service, Philadelphia, PA, US; 1985, Database accession No. PREV198681008845 XP002263605 & *American Review of Respiratory Disease*. 1985, pp. 576-581, vol. 132, No. 3.

Derksen et al., "Value of Radiology in the Diagnosis of Reflux Esophagitis," *Diagnostic Imaging in Clinical Medicine*, 1985, pp. 257-262, vol. 54, No. 5.

Elidemir et al., "A novel diagnostic method for pulmonary aspiration in a murine model: Immunocytochemical staining of milk proteins in alveolar macrophages," *American Journal of Respiratory and Critical Care Medicine*, Feb. 2000, pp. 622-626, vol. 161, No. 2, Part 1.

McVeagh et al., "Pulmonary Aspiration Studied by Radionuclide Milk Scanning and Barium Swallow Roentgenography," *American Journal of Diseases of Children*, 1987, pp. 917-921, vol. 141, No. 8.

* cited by examiner

Polylactic acid instilled animal

Saline instilled animal

DIAGNOSTIC MICROSPHERES

FIELD

The present invention relates to a diagnostic marker for the diagnosis of aspiration and gastroesophageal reflux in children and adults, to the manufacture of such markers and the use thereof.

BACKGROUND

Aspiration into the airways is one of the major causes of lung disease in infants and young children. Unfortunately the diagnosis of aspiration is often delayed due to unawareness and to the low sensitivity and specificity of existing diagnostic tests.

Aspiration of food or gastric material into the tracheobronchial tree can result in a variety of disease states such as laryngeal and tracheo-bronchial inflammation leading to stridor, cough, wheezing, recurrent pneumonia, bronchiectasis, pulmonary fibrosis and even suffocation and death due to massive aspiration (Mendelson C L. The aspiration of stomach contents into the lungs during obstetric anesthesia. *Am J Obstet Gynecol* 1946; 52: 191-205; Bauer M L, Figueroa-Colon, Georgeson K, Young D W. Chronic pulmonary aspiration in children. *South Med J* 1993; 86: 789-795; Moran T J. Experimental aspiration pneumonia. *Arch Pathol* 1955; 60: 122-129).

The common conditions that predispose to aspiration in infants and young children include prematurity due to developmental delay of the coordination between swallowing and breathing (Harding R. Johnson P, McClealand M E. Liquid sensitive laryngeal receptors in the developing ship cat and monkey. *J Physiol Lond* 1978; 277: 409-422), abnormal communication between airways and esophagus such as laryngo-tracheal cleft or tracheo-esophageal fistula, massive gastro-esophageal reflux, and neurological abnormalities such as cerebral palsy, vocal cord paralysis and familial dysautonomia.

The available tests for the diagnosis of aspiration such as barium swallow during videofluoroscopy and gastroesophageal scintigraphy are not sensitive enough (McVeagh P. Howman-Giles R, Kemp A. Pulmonary aspiration studied by radionuclide milk scanning and barium swallow roentgenography. *Am J Dis Child* 1987; 141: 917-921). In 1985, Corwin and Irwin (Corwin R W, Irwin R S. The lipid-laden alveolar macrophage as a marker of aspiration in parenchymal lung disease. *Am Rev Respir Dis* 1985; 132: 576-581) introduced the Oil-Red-O staining of lipid laden alveolar macrophages (LLAM) as a marker for aspiration. More recently, others have noticed that this test is not specific for aspiration and that other conditions can also result in an increase in fat vacuoles inside alveolar macrophages (Kajetanowicz A, Stinson D, Laybolt K S, Resch L. Lipid-laden macrophages in tracheal aspirate of ventilated neonates receiving intralipid. *Pediatr Pulmonol* 1999; 28: 101-108; Knauer-Fisher S, Ratjen F. Lipid-laden macrophages in bronchoalveolar lavage fluid as a marker for pulmonary aspiration. *Pediatr Pulmonol* 1999; 27: 419-422; Vichinsky E, Williams R, Das M, Earles A N, Lewis N, Adler A, McQuintty J. Pulmonary fat embolism: a distinct cause of severe acute chest syndrome in sickle cell anemia. *Blood* 1994; 11: 3107-3122).

Elidemir and his colleagues (Elidemir O, Fan L L, Colasurdo N. A novel diagnostic method for pulmonary aspiration in a murine model. Immunocytochemical staining of milk proteins in alveolar macrophages. *Am J Respir Crit Care Med* 2000; 161: 622-626) have recently shown that aspiration of milk in mice could be diagnosed by specific immunocytochemical staining of milk proteins in bronchoalveolar macrophages. Although this method seems to be specific for the detection of milk, aspiration of other food substances cannot be detected by this method. Furthermore they stained milk proteins ($\alpha$-lactalbumin and $\beta$-lactoglobulin) in alveolar macrophages by an immunocytochemical method. They found that their method is very sensitive and very specific as compared to Oil-Red O staining, but the stainings were positive only for the 3-4 days following induced aspiration. Aspiration can occur from above as in children with neurologic impairment, but may be secondary to gastro-esophageal reflux and may occur only during the massive episodes and not necessarily every day.

SUMMARY

It is therefore an object of the present invention to provide a sensitive and specific marker that could help diagnose aspiration that may have occurred days or weeks previously. As will be described and explained hereinafter the marker of the present invention is one that is safe and bio-degradable, can be given orally with food, can easily be "swallowed" by alveolar macrophages and can be identified in bronchoalveolar lavage (BAL) alveolar macrophages for a substantial period of time.

In a recent study (Avital A, Sherman Y, Springer C. Charcoal is a sensitive, specific and stable marker for the diagnosis of aspiration in hamsters. Pediatr Res 51:1-5, 2002) the present inventors used activated charcoal particles mixed with milk or normal saline and performed tracheal instillation in hamsters. Charcoal particles were easily identified in BAL for the three months following a single instillation, although hypercellularity was found in BAL after three months and it was attributed to the fact that some of the particles were large and may have induced airway inflammation.

As will be realized, charcoal particles were not suitable and would not be acceptable as a diagnostic tool for humans due to the danger inherent in introducing charcoal particles into the lungs.

With the above state of the art in mind, it is clear that there is a need for a safe diagnostic marker to detect both aspiration and gastroesophageal reflux for populations at risk such as the young pediatric and the geriatric population as well as those who suffer from neurological deficit leading to swallowing disturbances. As will be realized these groups are prone to aspiration of food to the lungs, which can result in severe lung damage and even death.

Figure 1:
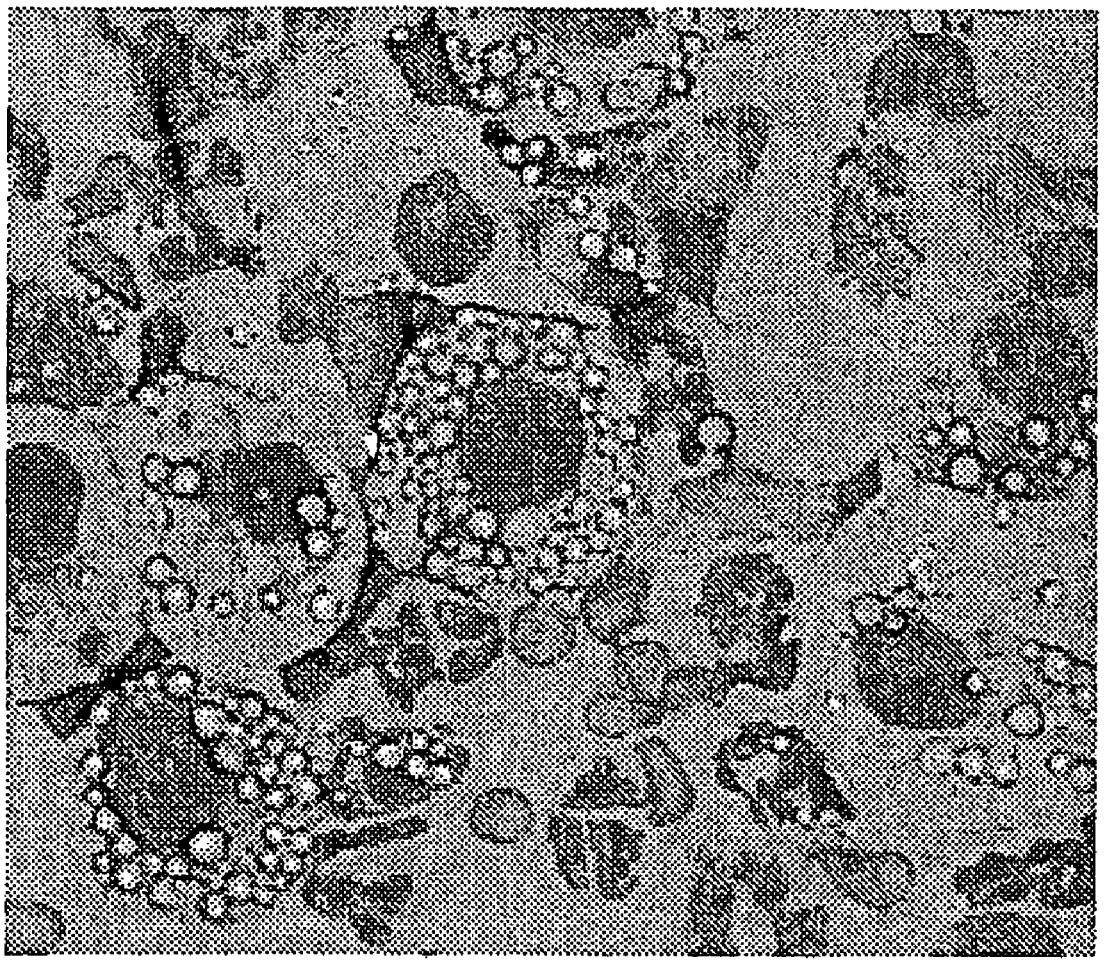
FIG. 1 is a photomicrograph showing polylactic acid instilled directly into the trachea of hamsters and detected inside alveolar macrophages obtained after whole lung lavage.

Thus according to the present invention there is now provided a diagnostic composition for detecting both aspiration and gastroesophageal reflux comprising biodegradable microspheres having a diameter of about 0.1-10 microns.

In preferred embodiments of the present invention said microspheres have a diameter of about 1-4 microns.

In especially preferred embodiments of the present invention there are provided diagnostic composition for detecting both aspiration and gastroesophageal reflux comprising biodegradable polymeric microspheres having a diameter of about 0.1-10 microns.

Any polymer, which is degradable via a hydrolytic and/or enzymatic mechanism, may be suitable. Polymers which undergo degradation under these conditions are, among others, polyesters, polyphosphate esters, polyphosphazenes, polyorthoesters, polyanhydrides, polycarbonates, polyamides and proteins (polypeptides). Typical polyesters are e.g. homopolymers or different copolymers of lactic acid (or lactide), glycolic acid (or glycolide), mandelic acid, caprolactone, $\alpha$-hydroxy acids (e.g. hydroxy butyric acid). Polymers containing optically active monomers, may consist of only d- or l-monomers, or any combination of the two. By varying the chemical composition and/or the molecular weight of the polymer, it is possible to control its degradation rate.

For any specific polymer or copolymer, different solvents, non-solvents and surfactants may be suitable in the preparation process thereof.

In another aspect of the present invention there is provided a food product containing a diagnostic composition for detecting both aspiration and gastroesophageal reflux said composition comprising biodegradable microspheres having a diameter of about 0.1-10 microns.

Especially preferred for use in the present invention are microspheres of polylactic acid.

As will be described hereinafter, according to the present invention there was performed tracheal instillation of small (2.1µ) and uniform polylactic acid microspheres suspended in a saline solution in hamsters, compared it to tracheal instillation of normal saline alone and followed for BAL cytology, microsphere index and lung histology during the following three months.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

Procedure of PLA Microspheres Preparation by Precipitation with a Non-Solvent 0.5 g of d,l-PLA (polylactic acid—Boehringer), of a molecular weight of either 2000 or 30000, were dissolved in 42 ml of acetone (Frutarom). 100 ml of distilled water were added dropwise, over a period of 60 minutes, under mild magnetic stirring. Spherical particles of PLA, 1-2 microns in diameter, are formed at an early stage in the process by precipitation. The acetone and part of the distilled water, were then evaporated by using a rotary evaporator (Buchi), at 40° C. At this stage, a surfactant (Pluronic F-68) is added to the suspension, at a concentration of 1.5%, in order to prevent aggregation and caking of particles following precipitation. It is worth mentioning that different surfactants and surfactant concentrations may be suitable for this purpose. Also, the method is tolerant to relatively large changes in the amount of both the acetone and distilled water.

Although the microspheres are easily visible by light microscopy, both with and without a polarizer, the possibility of coloring the microspheres was explored. The colorants, which are added to the acetone solution, should dissolve in acetone and be relatively hydrophobic, in order to be included inside the particles during the precipitation process. Alternatively, another indicator, such as a fluorescent material may be added.

Methods:

Animals: give number female Syrian hamsters (*Mesocricetus auratus*) 9-12 weeks old, weighing 100-140 g and obtained from Harlan Sprague Dawley (Indianapolis, USA), were used for the experiments. The study was approved by the local Institutional Animal Care and Use Committee.

give number hamsters were used as naive controls (without tracheal instillation).

give number hamsters had 0.1 ml tracheal instillation of either sterile normal saline (n=18) or white polylactic acid microspheres (n=24) of uniform size (2.1 µ). On days 1, 3, 10, 32, 60 and 90 after instillation, the animals were sacrificed (saline, n=3 and microspheres, n=4) and BAL was performed.

All microspheres were efficiently suspended (10 mg/ml) within sterile normal saline by sonification as shown by light microscopy.

Anesthesia: A mixture of ketamine HCl (50 mg/ml, 10 ml) and dehydrobenzperidol (2.5 mg/ml, 2 ml) was administered by intraperitoneal injection, 0.25 ml before tracheal instillation, and 0.4 ml before exsanguination and BAL. Tracheal instillation. Direct intubation was performed with a blunted metal needle. A few ventilations with a small ambu bag were given to ascertain intratracheal position of the needle by confirming chest movement. Normal saline or microsphere suspension (0.1 ml) was slowly instilled into the trachea, followed by a few ventilations with the ambu bag to disperse the fluid and to prevent apnea.

Bronchoalveolar lavage: On the planned BAL day under anesthesia, exsanguination was performed by transection of the abdominal aorta. The trachea was exposed and a blunted needle covered with a polyethylene cannula was inserted into the trachea. Three aliquots of 5 ml sterile 0.9% saline were injected and withdrawn with a total recovery of 85.3±0.8%. The fluid was examined for total cell counts and slides for differential counts were prepared on a Shandon Cytospin 3 (Cheshire, England) using approximately 100 µL of BAL fluid.

Microsphere index: The first 100 consecutive intact macrophages viewed were evaluated and the total number of white microspheres within the 100 macrophages was defined as the microsphere index on each BAL day.

Histology: Lungs from all animals were preserved in formaldehyde for further evaluation and four slides from both lungs were prepared. Other internal organs (kidneys, liver, spleen, adrenals, pancreas, heart and brain) from 8 hamsters after 90 days of tracheal instillation (5 following white microsphere instillation and 3 following saline instillation) were preserved in formaldehyde for further evaluation Animals instilled black microspheres had all extrapulmonary organs, including perihilar lymph glands, preserved in formaldehyde for histological evaluation. Two slides from each extrapulmonary organ were prepared. Hematoxylin-eosin was used for staining. Slides were thoroughly evaluated by two senior pathologists (V.D and Y.S.).

Statistics: Group data are expressed as mean±standard error (SE) of the mean. Differences between groups were compared using ANOVA with Bonferroni correction. Differences were taken as significant when p<0.05.

Figure 2:
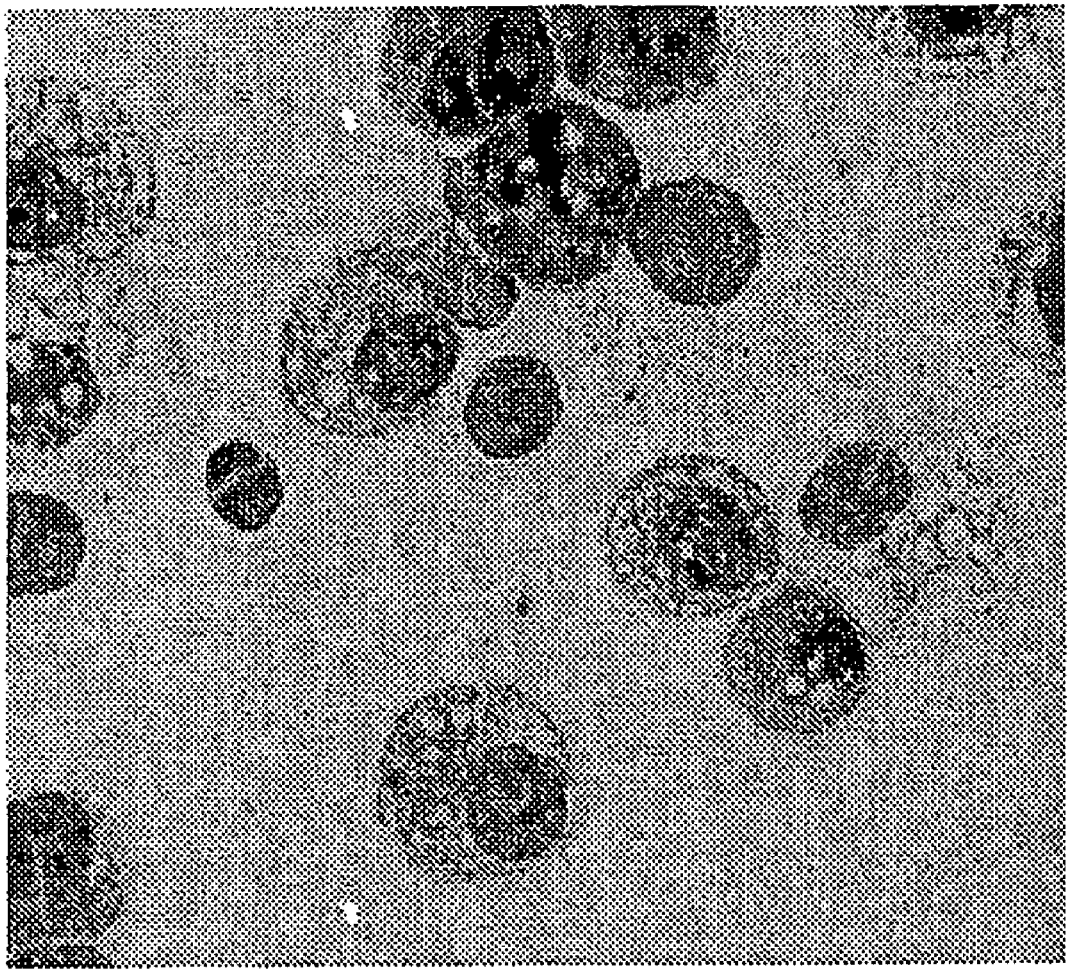
FIG. 2 is a photomicrograph showing alveolar macrophages of saline instilled animals.

Results:

The results of this experiment are shown in FIGS. 1 and 2 appended hereto in which FIG. 1 is a photomicrograph showing polylactic acid instilled directly into the trachea of hamsters and detected inside alveolar macrophages obtained after whole lung lavage and FIG. 2 is a photomicrograph showing alveolar macrophages of saline instilled animals.

As can be seen, the white microspheres of polylactic acid are clearly identified within the alveolar macrophages and therefore can be used as a specific sensitive and stable marker for the diagnosis of aspiration.

As will be realized, in addition to polylactic acid other polymers and copolymers as well as different solvents, non-solvents and surfactants are suitable in the preparation process of the microspheres for use in the present invention.

Examples of proteins, which may be used for this purpose are human albumin, hemoglobin, gelatin and soybean proteins.

EXAMPLE 2

Precipitation with a Non-Solvent

The procedure of Example 1 as described for PLA is repeated, except that the solvent is either water or an aqueous solution and the non-solvent is a water-soluble volatile solvent, such as acetone.

EXAMPLE 3

Interfacial Crosslinking Process 2.5 g of protein were dissolved in 35 ml of 0.1N NaOH solution (aqueous phase), under magnetic stirring. The protein solution was emulsified in 75 ml of cyclohexane (organic phase-Baker), containing 0.5% phosphatidylcholine (surfactant—Sigma), under 350 rpm mechanical stirring. A solution of 168.2 mg of succinylchloride (SC) (Sigma) in 38 ml cyclohexane was added dropwise to the emulsion, for a period of 45 minutes. SC reacts predominantly with the proteins amine groups via a condensation reaction mechanism, at room temperature. The microsphres were then separated by decantation, washed three times with acetone (Frutarom) and air dried.

The crosslinking agent can be any diacylchloride, or any di- or poly functional molecule able to react with the proteins chemically active groups. Using this method, either microspheres or microcapsules may be obtained. The rigidity of the microspheres may be controlled by changing the nature and concentration of the crosskinking agent, as well as the nature of the organic phase and rinsing solvents.

EXAMPLE 4

Denaturation by Heating

The protein is either precipitated as in Example 2, or emulsified as in Example 3, after which, the suspension is heated sufficiently to induce denaturation of the protein, thus stabilizing the particles.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A diagnostic method for detecting pulmonary aspiration or gastroesophageal reflux comprising:
   orally administering to a subject microspheres consisting of a bio-degradable polymer and having a diameter of about 0.1-10 microns, said microspheres containing no diagnostic indicator other than the bio-degradable polymer;
   obtaining bronchoalveolar lavage; and
   detecting the presence of said microspheres within alveolar macrophages obtained by said bronchoalveolar lavage.

2. A diagnostic method according to claim 1, wherein the composition is administered in combination with food.

3. A diagnostic method according to claim 1 for detecting pulmonary aspiration, wherein said polymeric microspheres are formed from polymeric materials selected from the group consisting of polyesters, polyphosphate esters, polyphosphazenes, polyorthoesters, polyanhydrides, polycarbonates and polyamides.

4. A diagnostic method according to claim 1, wherein said bio-degradable polymeric microspheres have a diameter of about 1-4 microns.

5. A diagnostic method according to claim 1, wherein said polymeric microspheres are formed from polyesters selected from the group consisting of homopolymers and copolymers of lactic acid, glycolic acid, mandelic acid, caprolactone, α-hydroxy acids, lactides and glycolides.

6. A diagnostic method according to claim 1, wherein said bio-degradable microspheres are formed of polylactic acid.

* * * * *